(12) United States Patent
Yang et al.

(10) Patent No.: US 12,098,410 B1
(45) Date of Patent: Sep. 24, 2024

(54) **RECOMBINANT *ZYMOMONAS MOBILIS* FOR PRODUCING ETHYLENE GLYCOL, METHOD AND USES THEREOF**

(71) Applicant: Hubei University, Wuhan (CN)

(72) Inventors: Shihui Yang, Wuhan (CN); Xiongying Yan, Wuhan (CN); Mian Li, Wuhan (CN); Xia Wang, Wuhan (CN); Qiaoning He, Wuhan (CN)

(73) Assignee: Hubei University, Wuhan (CN)

( * ) Notice: Subject to any disclaimer, the term of this patent is extended or adjusted under 35 U.S.C. 154(b) by 0 days.

(21) Appl. No.: 18/401,511

(22) Filed: Dec. 31, 2023

(30) Foreign Application Priority Data

Mar. 10, 2023 (CN) .......................... 202310246847.7

(51) Int. Cl.
| | | |
|---|---|---|
| *C12P 7/18* | (2006.01) | |
| *C12N 9/02* | (2006.01) | |
| *C12N 9/04* | (2006.01) | |
| *C12N 9/88* | (2006.01) | |
| *C12N 15/74* | (2006.01) | |

(52) U.S. Cl.
CPC .............. *C12P 7/18* (2013.01); *C12N 9/0006* (2013.01); *C12N 9/0008* (2013.01); *C12N 9/88* (2013.01); *C12N 15/74* (2013.01); *C12Y 101/01001* (2013.01); *C12Y 101/01175* (2013.01); *C12Y 102/01021* (2013.01); *C12Y 401/02* (2013.01); *C12Y 402/01082* (2013.01)

(58) Field of Classification Search
CPC ....... C12P 7/18; C12N 9/0006; C12N 9/0008; C12N 9/88; C12N 15/74; C12Y 101/01001; C12Y 101/01175; C12Y 102/01021; C12Y 401/02; C12Y 402/01082
See application file for complete search history.

(56) References Cited

U.S. PATENT DOCUMENTS

2017/0260551 A1   9/2017 Koch et al.

FOREIGN PATENT DOCUMENTS

CN    110358720 A    10/2019
CN    111500517 A    8/2020

OTHER PUBLICATIONS

Cabulong et al. (Appl Microbiol Biotechnol, 2018, 102:2179) (Year: 2018).*
Dong et al. (Biotechnol Bioeng, 2011, 108:1616) (Year: 2011).*
NCBI Accession No. NC_000913.3 Region 282278 (3 pages, Mar. 9, 2022) (Year: 2022).*
NCBI Accession No. NC_000913.3 Region 283201 (4 pages, Mar. 9, 2022) (Year: 2022).*
UniProt Accession No. H2VFM0_ZYMMO (1 page, Mar. 21, 2012) (Year: 2012).*
Kegg et al. (*Zymomonas mobilis* subsp. *mobilis* ZM4: ZMO1771, https://www.genome.jp/entry/zmo:ZMO1771, visited Jun. 3, 2024) (Year: 2024).*

* cited by examiner

*Primary Examiner* — David Steadman
*Assistant Examiner* — Joseph R Spangler
(74) *Attorney, Agent, or Firm* — Nitin Kaushik

(57) ABSTRACT

Recombinant *Zymomonas mobilis* for producing ethylene glycol, method and uses thereof are provided. The recombinant *Zymomonas mobilis* carries and expresses genes related to a synthesis pathway of xylonic acid and genes related to a synthesis pathway of ethylene glycol.

3 Claims, 10 Drawing Sheets
Specification includes a Sequence Listing.

RECOMBINANT *ZYMOMONAS MOBILIS* FOR PRODUCING ETHYLENE GLYCOL, METHOD AND USES THEREOF

CROSS-REFERENCE TO RELATED APPLICATIONS

This disclosure claims priority to Chinese Patent Application NO: 202310246847.7, filed with China Intellectual Property Office on Mar. 10, 2023, the entire contents of which are incorporated herein by reference.

SEQUENCE LISTING

The sequence listing xml file submitted herewith, named "WI_US23_12323_P_Sequence_Listing.xml", created on Apr. 18, 2024, and having a file size of 41,021 bytes, is incorporated by reference herein.

TECHNICAL FIELD

This disclosure relates to *Zymomonas mobilis*. Specifically, this disclosure relates to recombinant *Zymomonas mobilis* for producing ethylene glycol, method and uses thereof.

BACKGROUND

The statements herein provide background information relevant to the present disclosure only and do not necessarily constitute prior art.

Ethylene glycol, the simplest diol, is an economically important platform chemical that is steadily increasing in global demand and is widely used as a monomer for esterification and etherification of unsaturated polyester resins, polyethers and polyurethanes. A traditional two-step process is used for producing ethylene glycol. The process includes fermenting glucose to obtain ethanol, and chemically converting the ethanol to ethylene glycol. This process is inefficient, energy-consuming and environmentally unfriendly. Therefore, biosynthesis is a highly selective, low energy demand and environmentally friendly method for producing ethylene glycol. For example, metabolically engineered microorganisms, such as *Escherichia coli, Saccharomyces cerevisiae, Corynebacterium glutamicum* etc., are able to use xylose for producing ethylene glycol. However, the production process of these microorganisms are strictly aerobic, the cost of the production is high, and a large number of by-products would be produced.

*Zymomonas mobilis*, a natural ethanol-producing and facultative anaerobic Gram-negative bacterium, has unique Entner-Doudoroff (ED) metabolic pathway and high sugar fermentation efficiency. Moreover, as an ideal industrial cell factory, *Zymomonas mobilis* has the characteristics such as, high ethanol production, low biomass production, strong ethanol tolerance, high osmotic pressure resistance, and no need for additional oxygen during the fermentation process. At present, the production of PHB, 2, 3 butanediol, isobutanol and lactic acid have been realized in *Zymomonas mobilis*. Moreover, benefit by its high tolerance to lignocellulose hydrolysate, the production of ethanol from cellulose has already been commercialized in *Zymomonas mobilis*. Meanwhile, the mechanisms related to the tolerance of inhibitors in the lignocellulosic hydrolysates of *Zymomonas mobilis* has also been maturely studied. Additionally, by means of synthetic biology and metabolic engineering, *Zymomonas mobilis* could be modified into chassis cells that produce different platform compounds from the lignocellulosic hydrolysates.

SUMMARY

Embodiments disclose a recombinant strain from *Zymomonas mobilis* for producing ethylene glycol. The recombinant strain carries and expresses genes related to a synthesis pathway of xylonic acid and genes related to a synthesis pathway of ethylene glycol.

Embodiments disclose a recombinant plasmid for expressing ethylene glycol. The recombinant plasmid carries sequences of a gene xdh, a gene yagF, a gene yagE and a gene yqhD which are successively connected. Herein, the gene xdh is expressed with a promoter Ppdc. The gene yagF, the gene yagE and the gene yqhD are connected by a sequence of RBS and are expressed with a promoter Peno.

Embodiments disclose a recombinant plasmid for expressing ethylene glycol. The recombinant plasmid carries sequences of a gene xdh, a gene xylD, a gene yagE and a gene yqhD which are successively connected. Herein, the gene xdh is expressed with a promoter Ppdc. The gene xylD, the gene yagE and the gene yqhD are connected by using a sequence of RBS and are expressed with a promoter Peno.

Embodiments disclose a recombinant plasmid for expressing ethylene glycol. The recombinant plasmid carries sequences of a gene xdh, a gene yjhG, a gene yagE and a gene yqhD which are successively connected. Herein, the gene xdh is expressed by using a promoter Ppdc. The gene yjhG, the gene yagE and the gene yqhD are connected by using a sequence of RBS and are expressed with a promoter Peno.

Embodiments disclose a recombinant plasmid for expressing ethylene glycol. The recombinant plasmid carries sequences of a gene xdh, a gene yagF, a gene yagE and a gene fucO which are successively connected. Herein, the gene xdh is expressed by using a promoter Ppdc. The gene yagF, the gene yagE and the gene fucO are connected by using a sequence of RBS and are expressed with a promoter Peno.

Embodiments disclose a recombinant plasmid for expressing ethylene glycol. The recombinant plasmid carries sequences of a gene xdh, a gene yagF, a gene yagE and a gene ZMO1771 which are successively connected. Herein, the gene xdh is expressed by using a promoter Ppdc. The gene yagF, the gene yagE and the gene ZMO1771 are connected by using a sequence of RBS and are expressed with a promoter Peno.

Embodiments disclose a recombinant strain from *Zymomonas mobilis* for producing ethylene glycol. The recombinant strain has a transferred recombinant plasmid that carries a gene xdh, a gene yagF, a gene yagE and a gene yqhD.

Embodiments disclose a recombinant strain from *Zymomonas mobilis* for producing ethylene glycol. The recombinant strain has a transferred recombinant plasmid that carries a gene xdh, a gene xylD, a gene yagE and a gene yqhD.

Embodiments disclose a recombinant strain from *Zymomonas mobilis* for producing ethylene glycol. The recombinant strain has a transferred recombinant plasmid that carries a gene xdh, a gene yjhG, a gene yagE and a gene yqhD.

Embodiments disclose a recombinant strain from *Zymomonas mobilis* for producing ethylene glycol. The recombinant strain has a transferred recombinant plasmid that carries a gene xdh, a gene yagF, a gene yagE and a gene fucO.

Embodiments disclose a recombinant strain from *Zymomonas mobilis* for producing ethylene glycol. The recombinant strain has a transferred recombinant plasmid that carries a gene xdh, a gene yagF, a gene yagE and a gene ZMO1771.

Embodiments disclose a method of preparing recombinant strains from *Zymomonas mobilis* for producing ethylene glycol. The method includes overexpressing genes involved in a synthesis pathway of xylonic acid, and overexpressing genes involved in a synthesis pathway of ethylene glycol in *Zymomonas mobilis*. The genes involved in a synthesis pathway of xylonic acid include a gene xdh coding for xylose dehydrogenase. The genes involved in a synthetic pathway of ethylene glycol include coding genes yagF for xylonate dehydratase, yagE for aldolase, yqhD for glycolaldehyde reductase, xylD and yjhG for xylonate dehydratase, fucO and ZMO1771 for alcohol dehydrogenase.

Embodiments disclose a use of a recombinant strain from *Zymomonas mobilis* as embodiments described above for producing ethylene glycol.

Embodiments disclose a use of a recombinant strain prepared by the method as embodiments described above for producing ethylene glycol.

DETAILED DESCRIPTION OF THE EMBODIMENTS

Figure 1:
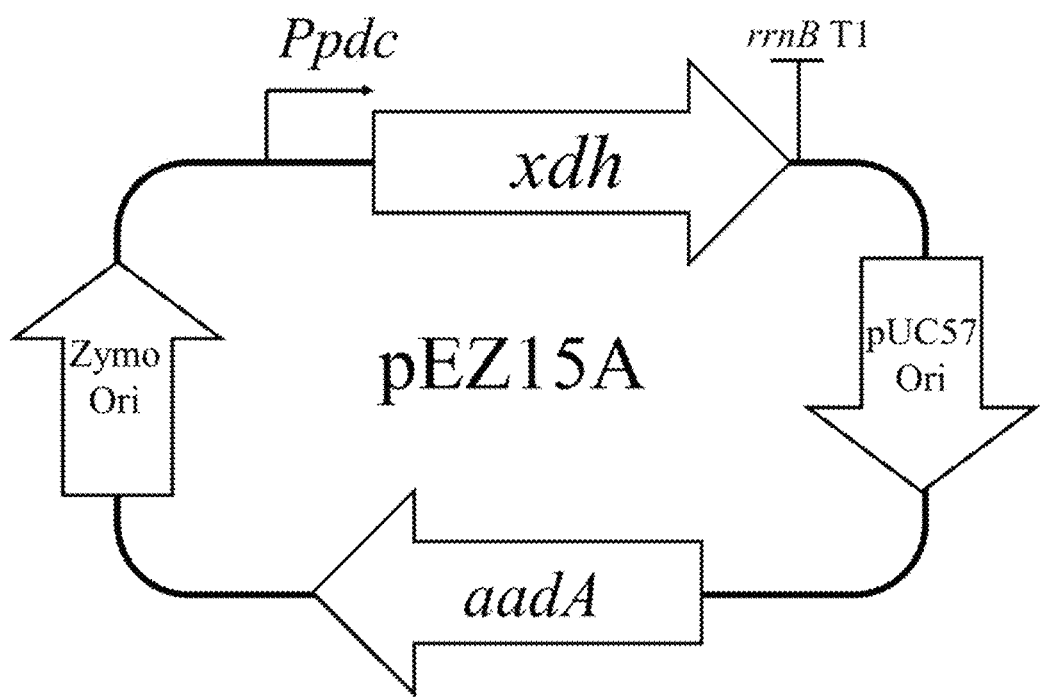
FIG. 1 depicts a schematic diagram of preparing a recombinant plasmid pXA1 according to embodiments.

Embodiments provides recombinant strains from *Zymomonas mobilis* for producing ethylene glycol. These recombinant strains are genetic *Zymomonas mobilis* ZM4s that carry and express genes related to synthesis pathways of xylonic acid and/or ethylene glycol. To solve the problem of oxygen demand of ethylene glycol's production, a Dahms Pathway, which takes xylonic acid as a main intermediate, is transferred into an original strain *Zymomonas mobilis* ZM4 to obtain recombinant strains in this disclosure. These recombinant strains are capable of producing ethylene glycol by utilizing xylose. And these recombinant strains are able to produce ethylene glycol with high yield in pure sugar mother liquor or toxic xylose mother liquor, by comparing xylonate dehydratase with glycolaldehyde reductase from different sources. The yield of ethylene glycol of these recombinant strains are able to reach 3.33 g/L fermentation broth.

These recombinant strains use their own powerful restriction-modification systems to have more antiviral capabilities than commonly engineered strains such as *E. coli*.

Since *Z. mobilis* is a facultative anaerobic microorganism, the fermentation of these recombinant strains based on *Z. mobilis* requires no dissolved oxygen control equipment, which can effectively reduce the production cost.

Since *Z. mobilis* is a growing and metabolically uncoupled microorganism, these recombinant strains based on *Z. mobilis* can efficiently convert the carbon source to the final metabolite ethanol, and are also suitable for producing other compounds with potentially high conversion rates.

In some embodiments, the xylonic acid synthesis pathway-related genes include a xylose dehydrogenase xdh gene.

In some embodiments, the ethylene glycol synthesis pathway-related genes include a coding gene yagF for xylonate dehydratase, a coding gene yagE for aldolase, a coding gene yqhD for glycolaldehyde reductase, coding genes xylD and yjhG for xylonate dehydratase, coding genes fucO and ZMO1771 for alcohol dehydrogenase.

Embodiments disclose a recombinant strain from *Zymomonas mobilis* for producing ethylene glycol. The recombinant strain has a transferred recombinant plasmid that carries a gene xdh, a gene yagF, a gene yagE and a gene yqhD.

Embodiments disclose a recombinant strain from *Zymomonas mobilis* for producing ethylene glycol. The recombinant strain has a transferred recombinant plasmid that carries a gene xdh, a gene xylD, a gene yagE and a gene yqhD.

Embodiments disclose a recombinant strain from *Zymomonas mobilis* for producing ethylene glycol. The recombinant strain has a transferred recombinant plasmid that carries a gene xdh, a gene yjhG, a gene yagE and a gene yqhD.

Embodiments disclose a recombinant strain from *Zymomonas mobilis* for producing ethylene glycol. The recombinant strain has a transferred recombinant plasmid that carries a gene xdh, a gene yagF, a gene yagE and a gene fucO).

Embodiments disclose a recombinant strain from *Zymomonas mobilis* for producing ethylene glycol. The recombinant strain has a transferred recombinant plasmid that carries a gene xdh, a gene yagF, a gene yagE and a gene ZMO1771.

This disclosure also provides recombinant plasmids for expressing ethylene glycol.

Figure 4:
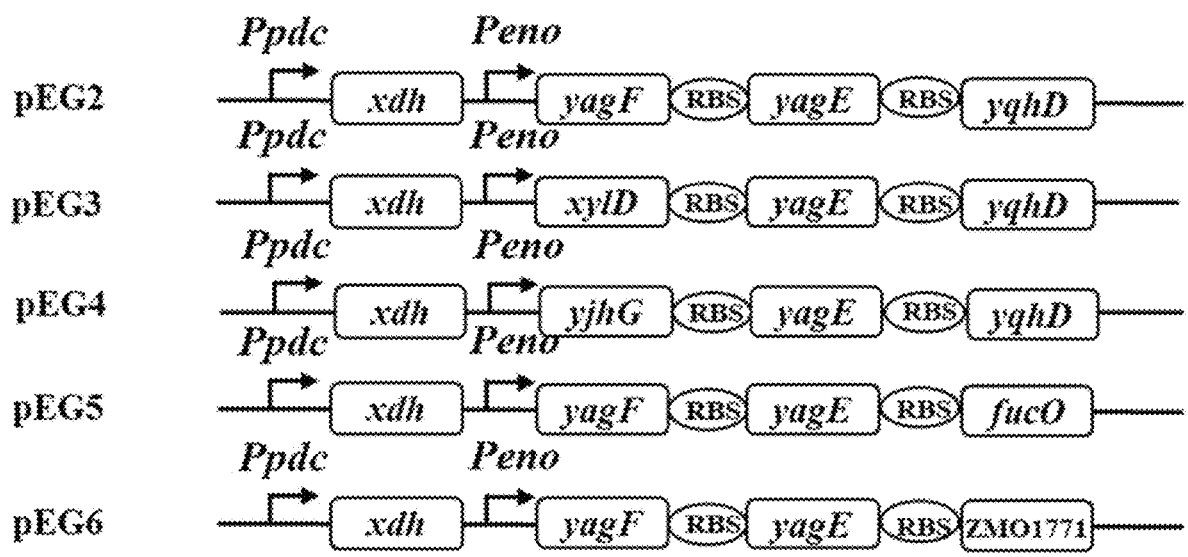
FIG. 4 depicts a schematic diagram of preparing five recombinant plasmids for ethylene glycol synthesis provided according to embodiments.

FIG. 4 shows a recombinant plasmid (pEG2) that carries a sequence of a gene xdh, a gene yagF, a gene yagE and a gene yqhD successively connected. Herein, the xdh is expressed with a promoter Ppdc. The gene yagF, the gene yagE and the gene yqhD are connected by an RBS and are expressed with a promoter Peno.

FIG. 4 shows a recombinant plasmid (pEG3) that carries a sequence of a gene xdh, a gene xylD, a gene yagE, and a gene yqhD successively connected Herein, the gene xdh is expressed with a promoter Ppdc. The gene xylD, the gene yagE, and the gene yqhD are connected with a sequence of RBS and are expressed with a promoter Peno.

FIG. 4 also shows a recombinant plasmid (pEG4) that carries a sequence of a gene xdh, a gene yjhD, a gene yagE and a gene yqhD successively connected. Herein, the gene xdh is expressed with a promoter Ppdc. The gene yjhD, the gene yagE and the gene yqhD are connected with a sequence of RBS and are expressed with a promoter Peno.

FIG. 4 also shows a recombinant plasmid (pEG5) that carries a sequence of a gene xdh, a gene yagF, a gene yagE and a gene fucO successively connected. Herein, the gene xdh is expressed with a promoter Ppdc. The gene yagF, the gene yagE and the gene fucO are connected with a sequence of RBS and are expressed with a promoter Peno.

FIG. 4 also shows a recombinant plasmid (pEG6) carries a sequence of a gene xdh, a gene yagF, a gene yagE and a gene ZMO1771 successively connected. Herein, the gene xdh is expressed with a promoter Ppdc. The gene yagF, the gene yagE and the gene ZMO1771 are connected with a sequence of RBS and are expressed with a promoter Peno.

Embodiments also provide a method of preparing recombinant strains from *Zymomonas mobilis* for producing ethylene glycol. The method includes: overexpressing genes involved in a synthetic pathway of xylonic acid in *Zymomonas mobilis*, and overexpressing genes involved in a synthetic pathway of ethylene glycol in *Zymomonas mobilis*. The genes involved in a synthetic pathway of xylonic acid include a gene xdh coding for xylose dehydrogenase. The genes involved in a synthesis pathway of ethylene glycol include coding genes yagF for xylonate dehydratase, yagE for aldolase, yqhD for glycolaldehyde reductase, xylD) and yjhG for xylonate dehydratase, fucO and ZMO1771 for alcohol dehydrogenase.

In some embodiments, recombinant plasmids have been constructed to overexpress genes involved in a synthetic pathway of xylonic acid, and genes involved in a synthesis pathway of ethylene glycol.

Some embodiments provide a method of preparing a recombinant strain from *Zymomonas mobilis* for producing ethylene glycol. The method includes: obtaining a promoter Ppdc, a gene xdh, a gene yagF, a gene yagE, a gene yqhD and a promoter Peno; connecting and inserting the promoter Ppdc and the gene xdh into a basal plasmid pEZ15A to obtain a plasmid for overexpressing xylose dehydrogenase; transferring the plasmid for overexpressing xylose dehydrogenase into *Zymomonas mobilis* ZM4 to obtain an intermediate strain; sequentially connecting the promoter Peno, the gene yagF, the gene yagE and the gene yqhD to obtain a fusion sequence, herein the gene yagF, the gene yagE and the gene yqhD are connected by a sequence of RBS; inserting the fusion sequence into the plasmid for overexpressing xylose dehydrogenase to obtain a recombinant plasmid; transferring the recombinant plasmid into the intermediate strain to obtain the recombinant strain.

Some embodiments provide a method of preparing a recombinant strain from *Zymomonas mobilis* for producing ethylene glycol. The method includes: obtaining a promoter Ppdc, a gene xdh, a gene xylD, a gene yagF, a gene yqhD and a promoter Peno; connecting and inserting the promoter Ppdc and the gene xdh into a basal plasmid pEZ15A to obtain a plasmid for overexpressing xylose dehydrogenase; transferring the plasmid for overexpressing xylose dehydrogenase into *Zymomonas mobilis* ZM4 to obtain an intermediate strain; sequentially connecting the promoter Peno, the gene xylD, the gene yagE and the gene yqhD to obtain a fusion sequence, herein the gene xylD, the gene yagE and the gene yqhD are connected by a sequence of RBS; inserting the fusion sequence into the plasmid for overexpressing xylose dehydrogenase to obtain a recombinant plasmid; transferring the recombinant plasmid into the intermediate strain to obtain the recombinant strain.

Some embodiments provide a method of preparing a recombinant strain from *Zymomonas mobilis* for producing ethylene glycol. The method includes: obtaining a promoter Ppdc, a gene xdh, a gene yjhG, a gene yagE, a gene yqhD and a promoter Peno; connecting and inserting the promoter Ppdc and the gene xdh into a basal plasmid pEZ15A to obtain a plasmid for overexpressing xylose dehydrogenase; transferring the plasmid for overexpressing xylose dehydrogenase into *Zymomonas mobilis* ZM4 to obtain an intermediate strain; sequentially connecting the promoter Peno, the gene yjhG, the gene yagE and the gene yqhD to obtain a fusion sequence, herein the gene yjhG, the gene yagE and the gene yqhD are connected by a sequence of RBS; inserting the fusion sequence into the plasmid for overexpressing xylose dehydrogenase to obtain a recombinant plasmid; transferring the recombinant plasmid into the intermediate strain to obtain the recombinant strain.

Some embodiments provide a method of preparing a recombinant strain from *Zymomonas mobilis* to producing ethylene glycol. The method includes: obtaining a promoter Ppdc, a gene xdh, a gene yagF, a gene yagE, a gene fucO and a promoter Peno; connecting and inserting the promoter Ppdc and the gene xdh into a basal plasmid pEZ15A to obtain a plasmid for overexpressing xylose dehydrogenase; transferring the plasmid for overexpressing xylose dehydrogenase into *Zymomonas mobilis* ZM4 to obtain an intermediate strain; sequentially connecting the promoter Peno, the gene yagF, the gene yagE and the gene fucO to obtain a fusion sequence, herein the gene yagF, the gene yagE and the gene fucO are connected by a sequence of RBS; inserting the fusion sequence into the plasmid for overexpressing xylose dehydrogenase to obtain a recombinant plasmid; transferring the recombinant plasmid into the intermediate strain to obtain the recombinant strain.

Some embodiments provide a method of preparing a recombinant strain from *Zymomonas mobilis* for producing ethylene glycol. The method includes: obtaining a promoter Ppdc, a gene xdh, a gene yagF, a gene yagE, a gene ZMO1771 and a promoter Peno; connecting and inserting the promoter Ppdc and the gene xdh into a basal plasmid pEZ15A to obtain a plasmid for overexpressing xylose dehydrogenase; transferring the plasmid for overexpressing xylose dehydrogenase into *Zymomonas mobilis* ZM4 to obtain an intermediate strain; sequentially connecting the promoter Peno, the gene yagF, the gene yagE and the gene ZMO1771 to obtain a fusion sequence, herein the gene yagF, the gene yagE and the gene ZMO1771 are connected by a sequence of RBS; inserting the fusion sequence into the plasmid for overexpressing xylose dehydrogenase to obtain a recombinant plasmid; transferring the recombinant plasmid into the intermediate strain to obtain the recombinant strain.

Embodiments of this disclosure also provide uses of these recombinant plasmids of *Z. mobilis* described above for producing ethylene glycol.

Embodiments of this disclosure also provide uses of these methods of preparing these recombinant plasmids of *Z. mobilis* described above for producing ethylene glycol.

The present disclosure will be illustrated below with more specific examples, but is not construed as limiting the embodiments of this disclosure.

Example 1: Prepare an Intermediate Strain (*Z. mobilis* XA1)

One important step of the synthesis from xylose to ethylene glycol is the synthesis of xylonic acid. And the synthesis from xylose to xylonic acid is achieved through expressing of a coding gene of xylose dehydrogenase derived from *Paraburkholderia xenovorans* and an enzymatic reaction. *Z. mobilis* XA1 can be prepared by transferring a plasmid pXA1 shown in FIG. 1 into *Z. mobilis*, and controlling the expression of xylose dehydrogenase with a strong promoter.

(1) Prepare the Plasmid pXA1

A sequence of gene xdh (shown in SEQ ID NO. 1, derived from *Paraburkholderia xenovorans*) and a sequence of strong promoter Ppdc (shown in SEQ ID NO. 2, derived from the genome of *Zymomonas mobilis* ZM4) were amplified by PCRs respectively. A basal plasmid pEZ15A (Yang, S. et al. (2016). Metabolic engineering of *Zymomonas mobilis* for 2, 3-butanediol production from lignocellulosic biomass sugars. Biotechnology for biofuels, 9(1), 189.) was amplified in reverse by a PCR.

Herein, the PCR procedure was set as: 98° C. pre-denaturation for 2 min; 98° C. denaturation for 10s, 55° C. annealing for 10s, 72° C. extension (set according to fragment length at 10s/kb) for a total of 30 cycles; 72° C. for 5 min after the end of the cycle reaction. The PCR product was stored at −20° C. after purification. And the other conditions of PCR were set as follows:

TABLE 1

PCR reaction system for sequence of gene xdh

| Component | Dosage(μL) |
|---|---|
| F-primer (10 μM) | 0.5 |
| R-primer (10 μM) | 0.5 |
| PRIMESTAR ® DNA Polymerase (Takara) | 10 |
| Template (5~10 ng) | X |
| ddH$_2$O | To 20 |
| Total volume | 20 |

Primers:
Ppdc-F: attcgcggccgcttctagagtatcgctcatgatcgeggcat, SEQ ID NO. 3
Ppdc-R: ggatagctcaacagatacattgcttactccatatattcaaaacactatgtctgaatc, SEQ ID NO. 4 Xdh-F: atgtatctgttgagctatccggaacag, SEQ ID NO. 5
Xdh-R: ttattcaccataccaaccagcatcaacaaaa, SEQ ID NO. 6

A fragment of xdh was mixed with a fragment of the basal plasmid pEZ15A in a ratio of 3:1 and configured to a reaction system as shown in Table 2. After 5 minutes of ice bath, the production of reaction was transferred to competent cells of *E. coli* by a general process.

Positive colonies were picked on plates with containing Spectinomycin. Subsequently, these positive colonies were verified by colony PCRs with primers 15A-fwd (gtaaaacgacggccagt, SEQ ID NO. 7)/15A-rev (gtcatagctgtttcctg, SEQ ID NO. 8). A procedure of the colony PCR was set as: 98° C. pre-denaturation for 3 min; 98° C. denaturation for 10s, 55° C. annealing for 10s, 72° C. extension for 80s for 30 cycles. The bands of the colony that was consistent with the expectations, were then verified by sequencing. Finally, the plasmid pXA1 could be extracted from the verified positive clones.

TABLE 2

Ligation reaction system of xdh with pEZ15A

| Component | Dosage |
|---|---|
| fragment of xdh | 0.12 pM |
| pEZ15A | 0.04 pM |
| 10 × Buffer 4 (Thermo) | 0.5 μL |
| T5 Exonuclease | 0.5 U |
| ddH$_2$O | To 5 μL |

(2) Prepare the Intermediate Strain

The process of preparing the intermediate strain included preparing competent cells of *Z. mobilis* ZM4 (*Z. mobilis* subsp. *mobilis* ZM4 ATCC3182, ATCC). 100 μL frozen bacteria of *Z. mobilis* ZM4 was removed from a −80° C. refrigerator firstly, and inoculated into 1 mL RMG5 loaded in a freezing tube and culturing at 30° C. to activate the strain. After the culture became cloudy, the cloudy culture was shifted into 200 mL liquid medium RMG5 loaded in a 250 ml bottle with blue cover, and the initial OD 600 nm was set within 0.025~0.3 in a 30° C. incubator. When OD600 nm of the culture exceeded 0.3, the bacteria was collected by centrifugation of 100 rpm at room temperature. The bacteria was washed once with sterile water and twice with 10% glycerin, and was slowly resuspended with 1-2 mL 10% glycerin, and finally 55 μL bacteria was packed into one 1.5 mL EP tube.

The process of preparing the intermediate strain also included the transfer of the plasmid pXA1 into the competent cells. Firstly, 1 mg of the plasmid pXA1 was added and gently mixed into 55 μL competent cells loaded in a 1.5 mL EP tube, and shifted into a 1 mm electroporation cuvette. And then the electroporation cuvette was placed into an electroporation instrument to electro-transfer. Herein, the electro-transformation conditions were set as: 200Ω, capacitor: 25 μF, voltage: 1.6 KV. And 1 mL RMG5 of liquid medium was added into the electroporation cuvette after electro-transferring, mixed well and then shifted to a sterile EP tube, sealed and incubated in a 30° C. thermostatic incubator for 4~6 h to get the transferred strains. And 100 μL of the transferred strains solution was evenously coated on a plate (that is plate containing 100 μg/mL Spectinomycin in RMG5, named RMG5+Spe); sealed and anastrophic incubated in a 30° C. thermostatic incubator.

Positive colonies were picked and verified by colony PCR with primers 15A-fwd and 15A-rev. The reaction system and procedure of the colony PCR were set as same as the above steps. The positive clones were activated in the medium of RMG5+Spe, and preserved by glycerin.

(3) Test of Yield of Xylonic Acid for the Intermediate Strain

The intermediate strain XA1 was activated in medium RMG5, and cultivated to get the seeds. The seeds were inoculated into a fermentation medium (named rich medium, RM, 10 g/L yeast extract, 20 g/L Glucose, 20 g/L Xylose, 2 g/L KH$_2$PO$_4$), and fermented at 30° C., 100 rpm, and added antibiotic(spectinomycin) with a final concentration of 100 g/mL if necessary.

The fermentation broth was centrifuged, and the supernatant was filtered by a 0.2 μm filter into an HPLC vial. The yield of xylonic acid for the intermediate strain XA1 was tested by a HPLC system (Shimadzu, Japan) consisting of BIO-RAD AMINEX® HPX-87H column (Bio-Rad, Hercules, CA, USA), a refractive index detector (RID) and a UV-detector. Herein, the temperature of column was set at 60° C., and 5 mM $H_2SO_4$ of solution was used as the mobile phase at a flow rate of 0.5 mL/min.

Figure 2A:
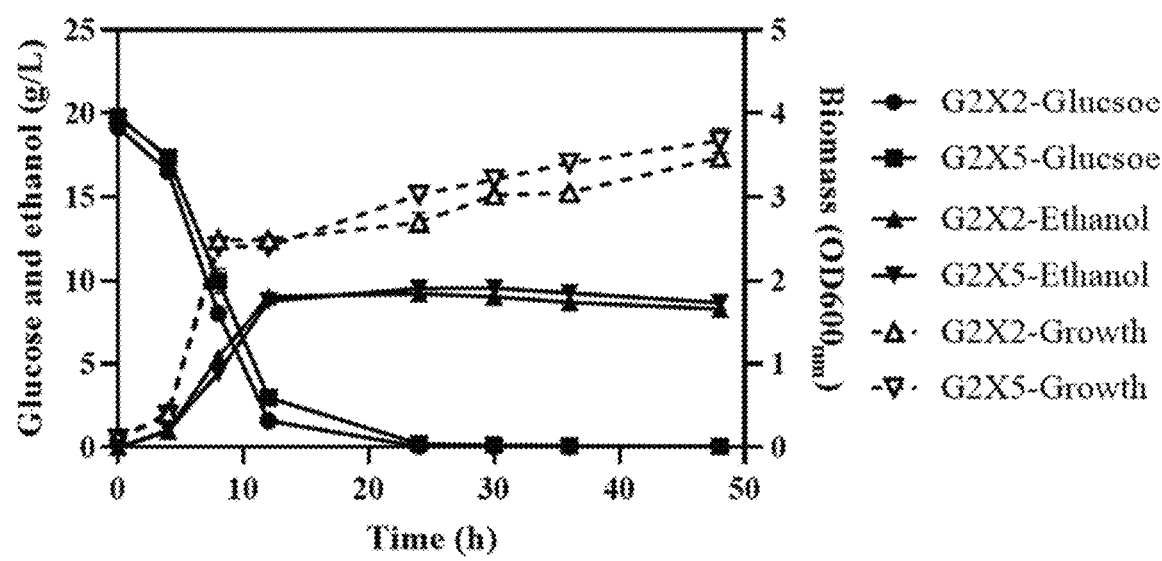
FIG. 2A shows test results of glucose consumption and ethanol production without $CaCO_3$ by an intermediate strain (*Z. mobilis* XA1) according to embodiments.
Figure 2B:
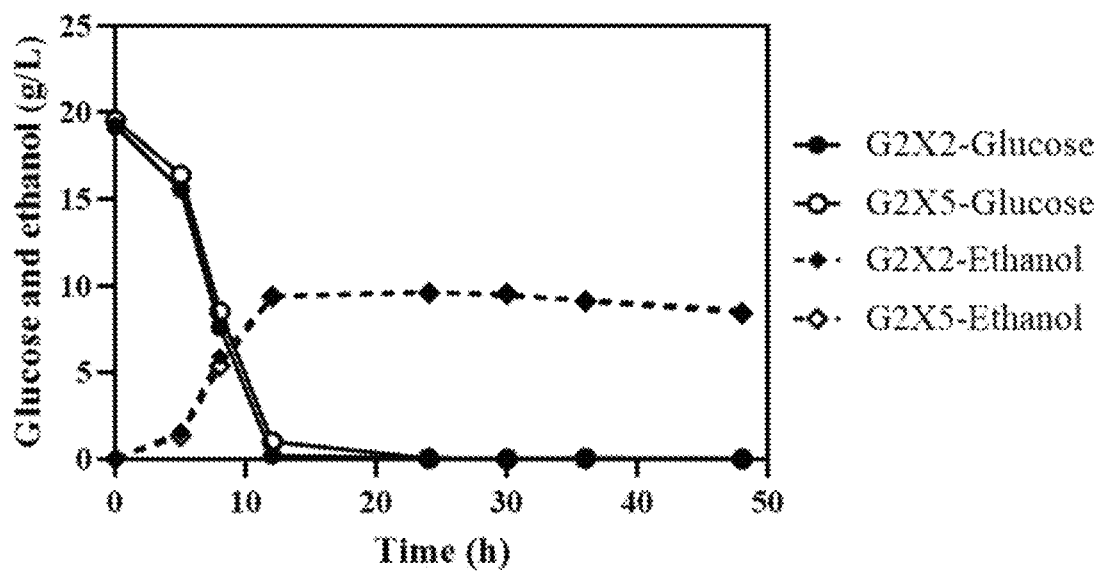
FIG. 2B shows test results of glucose consumption and ethanol production with $CaCO_3$ by an intermediate strain (*Z. mobilis* XA1) according to embodiments.
Figure 2C:
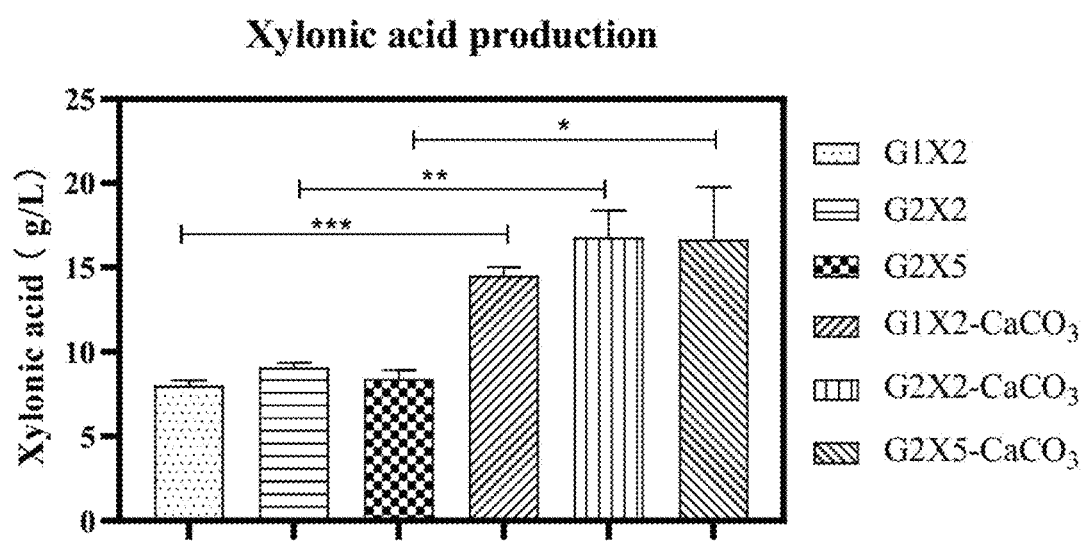
FIG. 2C shows test results of producing xylonic acid by an intermediate strain (*Z. mobilis* XA1) according to embodiments.
Figure 2D:
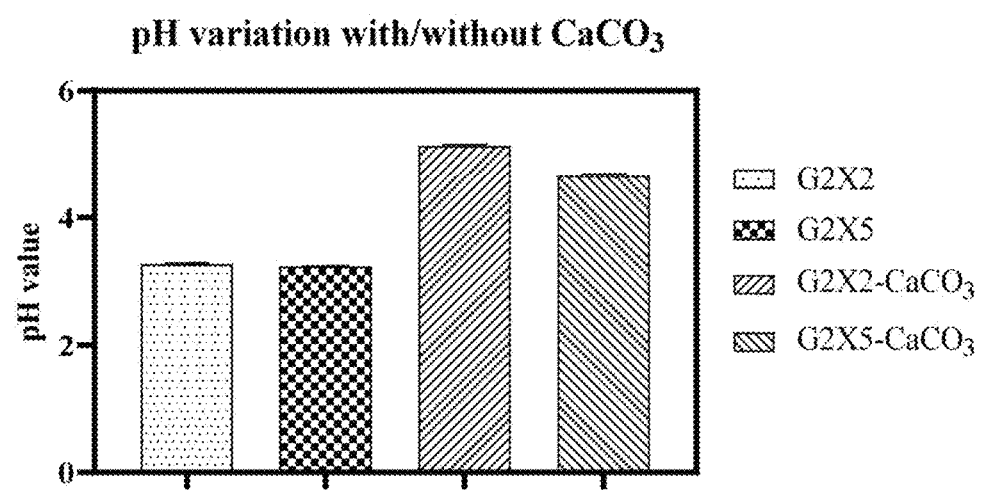
FIG. 2D shows test results of pH variation with or without $CaCO_3$ of an intermediate strain (*Z. mobilis* XA1) according to embodiments.

A fermentation of complete glucose consumption for 48h in RMG2X2 medium could generate 9.67±0.01 g/L of ethanol and 9.08±0.275 g/L of xylonic acid as shown in FIG. 2A. The production of xylonic acid during the fermentation of the strain XA1 would be inhibited at the mercy of a low pH (for example 3.0) as shown in FIG. 2D. For reducing the effect of pH on the fermentation performance of the strain, $CaCO_3$ would be added to neutralize the produced xylonic acid. By adding $CaCO_3$, the strain XA1 could completely consume glucose in the medium after 12 h of fermentation, and the ethanol yield reached the maximum, and the yield of xylonic acid was significantly different at 16.78±1.58 g/L, which was much higher than the condition of no adding $CaCO_3$ (FIG. 2B, FIG. 2C).

Example 2: Prepare a Recombination Strain for Producing Ethylene Glycol

Figure 3:
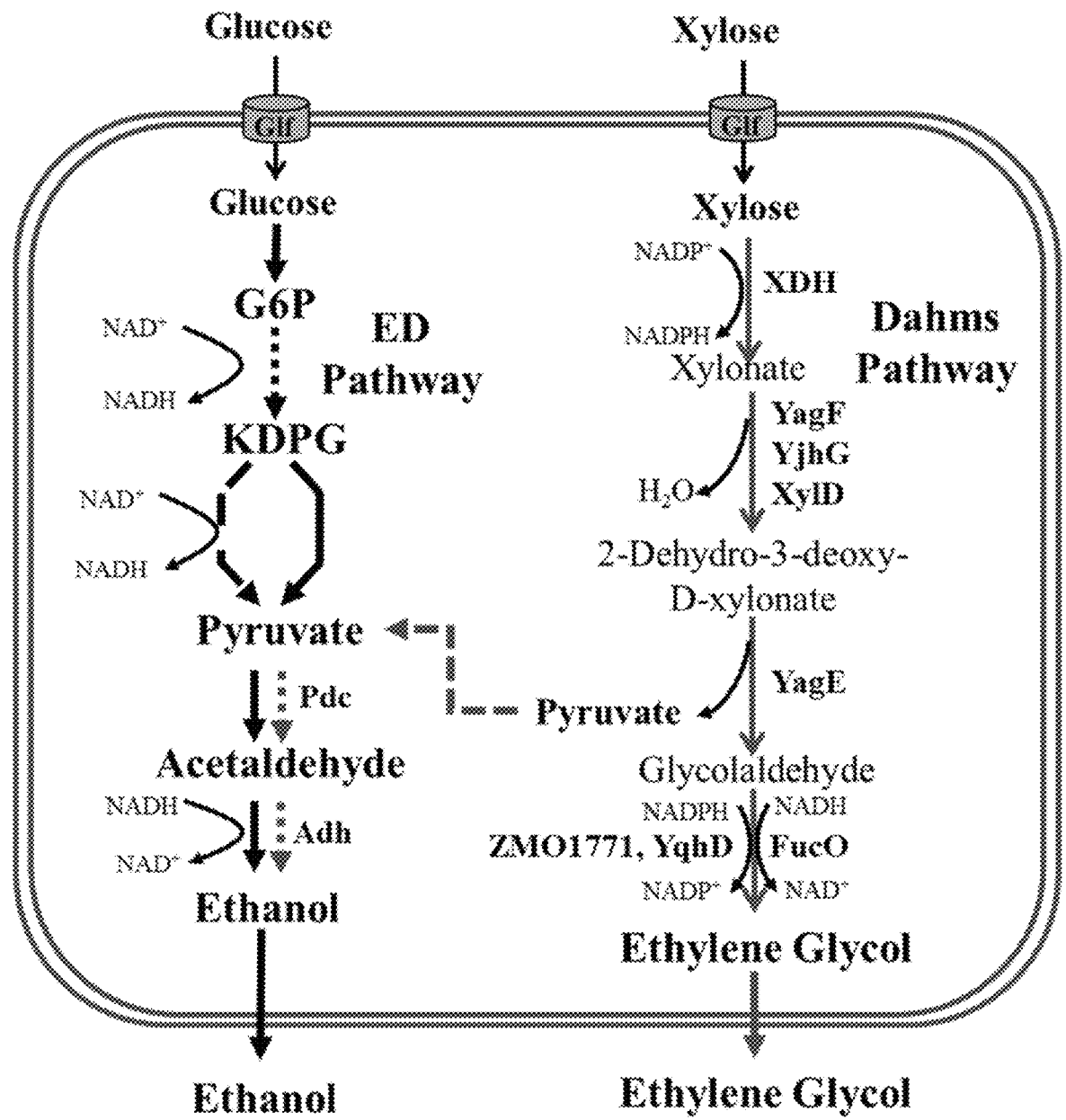
FIG. 3 depicts a Dahms pathway of preparing a recombinant strain EG2 from *Zymomonas mobilis* provided according to embodiments.

To further convert xylonic acid to ethylene glycol, an artificially designed Dahms pathway was introduced into the intermediate strain (Z. mobilis XA1) as shown in FIG. 3. In this process, a gene yagF and a gene yjhG for coding xylonate dehydratase derived from E. coli, and a gene yagE derived from E. coli for coding aldolase, and a gene yqhD and a gene fuco derived from different E. coli for coding aldehyde dehydrogenase, and a gene ZMO1771 from Z. mobilis for coding aldehyde dehydrogenase ZMO1771 were identified and tested.

(1) Prepare Recombinant Plasmids yagF (SEQ ID NO. 9), yagE (SEQ ID NO. 10), yqhD (SEQ ID NO. 11), xylD (SEQ ID NO. 12), yjhG (SEQ ID NO. 13), fucO (SEQ ID NO. 14), ZMO1771 (SEQ ID NO. 15) and a promoter Peno (SEQ ID NO. 16) were amplified by PCRs. Three genes (shown in FIG. 4, pEG2: yagF, yagE and yqhD; pEG3: xylD, yagE and yqhD; pEG4: yjhG, yagE and yqhD; pEG5: yagF, yagE and fucO; pEG6: yagF, yagE and ZMO1771) were respectively connected by PCRs with a sequence of RBS to get five connectors. Herein, the expressions of these three genes in the five connectors were respectively controlled by the promoter Peno. The five connectors were integrated respectively into the plasmid XA1 to assemble and construct five recombinant plasmids (pEG2~pEG6) as shown in FIG. 4.

The PCR procedure was set as: 98° C. pre-denaturation for 2 min; 98° C. denaturation for 10s, 55° C. annealing for 10s, 72° C. extension (set according to fragment length at 10s/kb) for a total of 30 cycles; 72° C. for 5 min after the end of the cycle reaction. And the product of PCR was stored at −20° C. after purification. And the PCR reaction system was set as Table 3.

TABLE 3

| PCR reaction system of yagF, yagE, yqhD, xylD, yjhG, fucO, ZMO1771 | |
|---|---|
| component | dosage(µL) |
| F-primer (10 µM) | 0.5 |
| R-primer (10 µM) | 0.5 |
| PRIMESTAR ® DNA Polymerase (Takara) | 10 |

TABLE 3-continued

| PCR reaction system of yagF, yagE, yqhD, xylD, yjhG, fucO, ZMO1771 | |
|---|---|
| component | dosage(µL) |
| Template (5-10 ng) | X |
| $ddH_2O$ | To 20 |
| Total volume | 20 |

Primers:
  Peno-F: tgtctatactccagttactcaatacgtaacaataatcagtt-tatcctaac, SEQ ID NO. 17
  Peno-R: atcgaaaccttcttaaaatcttttagacgag, SEQ ID NO. 18
  yagF-F: attttaagaaaggtttcgatatgaccattgagaaaattttcaccccg, SEQ ID NO. 19
  yagF-R: ggcattttctcctctttaatttaaattccgagcgcttttttaccgg, SEQ ID NO. 20
  yagE-F: tttaaattaaagaggagaaaatgccgcagtccgcgttg, SEQ ID NO. 21
  yagE-R: ttcattttctcctctttaattcagcaaagcttgagctgttgca, SEQ ID NO. 22
  yqhD-F: gctgaattaaagaggagaaaatgaacaactt-taatctgcacacccc, SEQ ID NO. 23
  yqhD-R: cageggccgctactagtttagegggcggcttcgtatatac, SEQ ID NO. 24
  xylD-F: attttaagaaaggtttcgatatgagcaatcgcaccccg, SEQ ID NO. 25
  xylD-R: ggcattttctcctctttaatttaatgattatgacgcggcaatttagcc, SEQ ID NO. 26
  yjhG-F: attttaagaaaggtttcgatatgtctgttcgcaatattttttgctgacg, SEQ ID NO. 27
  yjhG-R: ggcattttctcctctttaattcagtttttattcataaaat-egcgcaaagcc, SEQ ID NO. 28
  fucO-F: gctgaattaaagaggagaaaatggctaacagaatgattct-gaacgaaacg, SEQ ID NO. 29
  fucO-R: cageggccgctactagtttaccaggcggtatggtaaagctcta, SEQ ID NO. 30
  ZMO1771-F: gctgaattaaagaggagaaaatgctcaattttgattat-tataatccgacccatattg, SEQ ID NO. 31
  ZMO1771-R: cageggccgctactagttta-caagcttgcaagcagaatagcg, SEQ ID NO. 32

(2) Prepare Five Recombinant Strains

The transformation of the five recombinant plasmids (pEG2~pEG6) to get five recombinant strains (EG2~pEG6) and the screening of the five recombinant strains were consistent with the construction of the intermediate strain.

(3) Test for the Production of Ethylene Glycol of the Recombinant Strains

Strains of EG2~EG6 were fermented respectively in a rich medium (named RMG2X2, with containing 10 g/L yeast extract, 20 g/L Glucose, 20 g/L Xylose and 2 g/L $KH_2PO_4$) at 30° C., 100 rpm. And spectinomycin would be added at the final concentration of 100 µg/mL if necessary.

The fermentation broth was centrifuged, and the supernatant was filtered by a 0.2 µm filter into an HPLC vial. The yield of ethylene glycol for the five recombinant strains (EG2~pEG6) were tested by a HPLC system (Shimadzu, Japan) consisting of BIO-RAD AMINEX® HPX-87H column (Bio-Rad, Hercules, CA, USA), a refractive index detector (RID) and a UV-detector. Herein, the temperature of column was set at 60° C., and 5 mM $H_2SO_4$ of solution was used as the mobile phase at a flow rate of 0.5 mL/min.

Figure 5:
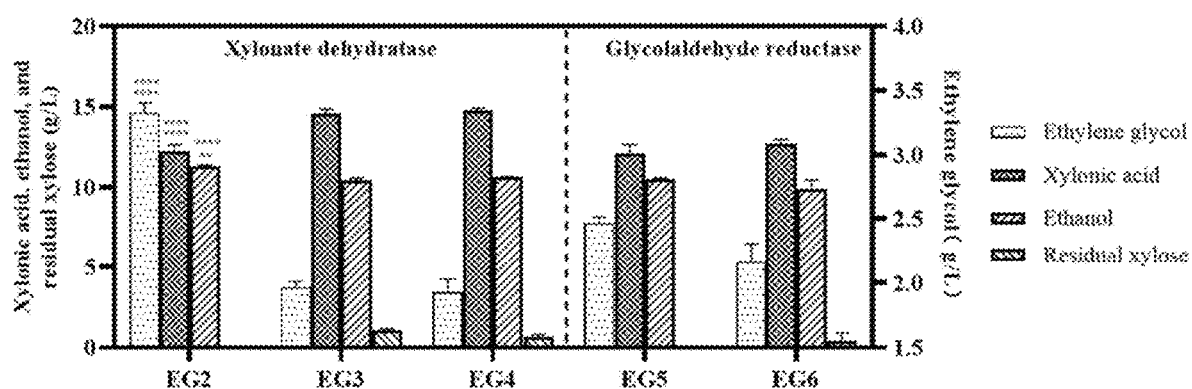
FIG. 5 shows the test results of fermenting property of five recombinant strains for ethylene glycol synthesis provided according to embodiments.

The yield of ethanol, ethylene glycol and xylonic acid of the five recombinant strains (EG2~EG6) were tested under equal conditions. As shown in FIG. 5 and Table 4, the gene yagF coding for xylonate dehydratase and the gene yqhD coding for aldehyde dehydrogenase, could able to give the recombinant strains with best effect for producing the ethylene glycol.

TABLE 4

Test of fermenting property for EG2~pEG6

| Strains | Consumption (g/L) | | Yield (g/L) | | |
|---|---|---|---|---|---|
| | glucose | xylose | ethylene glycol | xylonic acid | ethanol |
| EG2 | 19.41 ± 0.07 | 20.36 ± 0.06 | 3.26 ± 0.07 | 17.88 ± 0.08 | 10.13 ± 0.27 |
| EG3 | 20.20 ± 0.13 | 21.13 ± 0.20 | 1.97 ± 0.04 | 12.26 ± 0.39 | 11.32 ± 0.03 |
| EG4 | 20.12 ± 1.18 | 21.23 ± 0.04 | 1.93 ± 0.10 | 14.59 ± 0.26 | 10.43 ± 0.14 |
| EG5 | 18.24 ± 0.19 | 20.39 ± 0.12 | 2.47 ± 0.05 | 14.74 ± 0.17 | 10.65 ± 0.02 |
| EG6 | 18.26 ± 0.12 | 20.84 ± 0.12 | 2.17 ± 0.14 | 12.13 ± 0.52 | 10.41 ± 0.22 |

Example 3: Test of Recombinant Strain (EG2) in Mother Liquid Containing Xylose

Figure 6A:
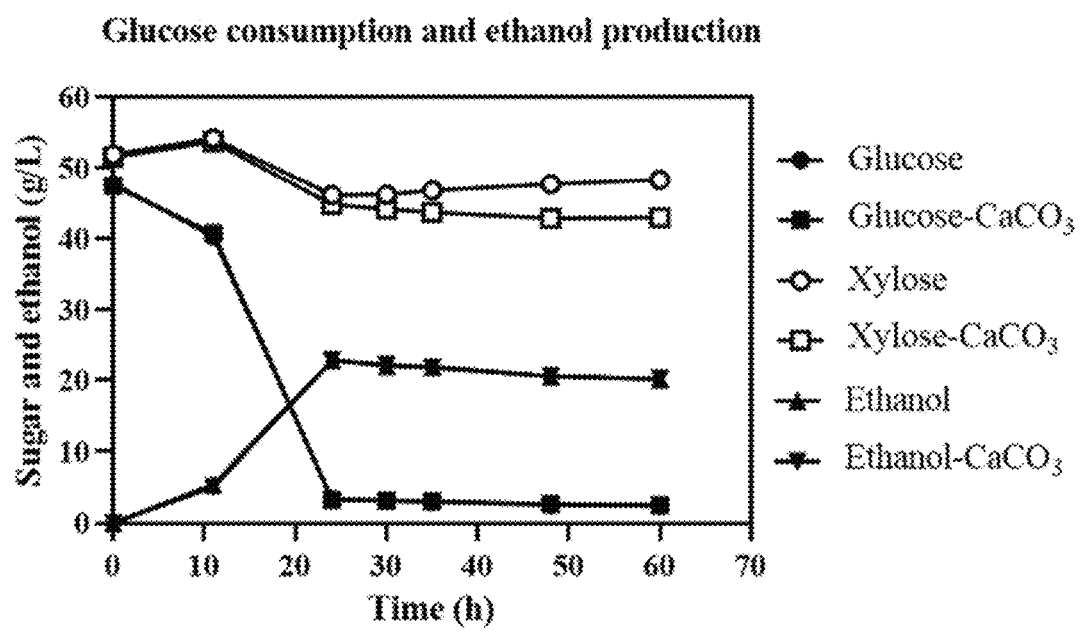
FIG. 6A shows test results of glucose consumption and ethanol production of a recombinant strain *Zymomonas mobilis* EG2 in xylose mother liquor according to embodiments.
Figure 6B:
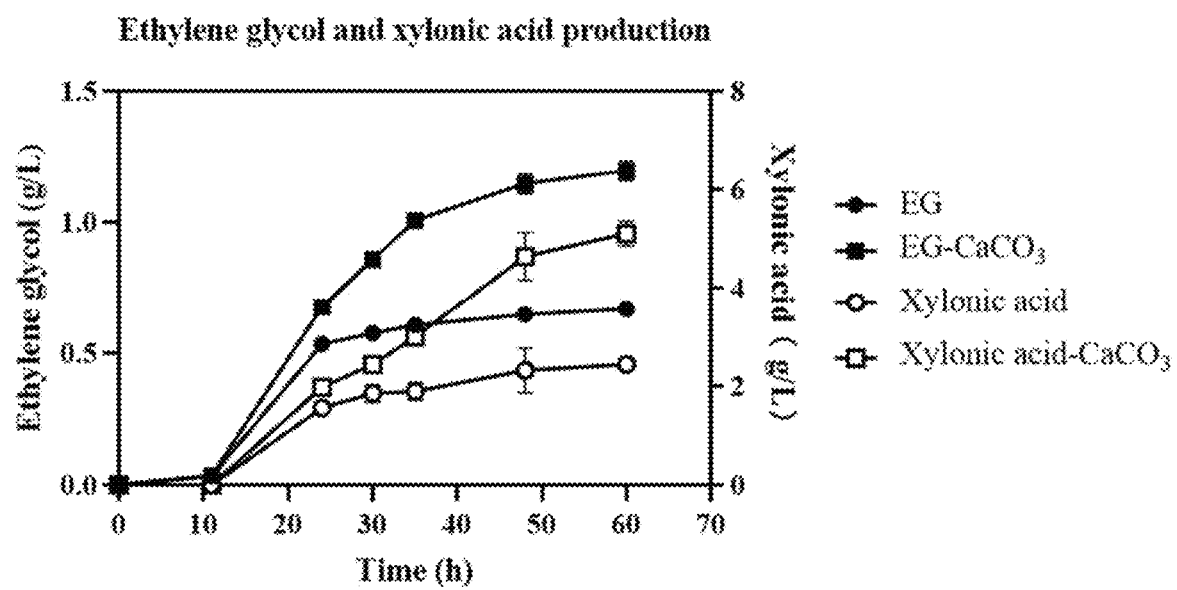
FIG. 6B shows test results of productions of ethylene glycol and xylonic acid of a recombinant strain *Zymomonas mobilis* EG2 in xylose mother liquor according to embodiments.

EG2 was activated and cultivated to obtain a seed solution. The seed solution was inoculated to 40 mL of fermentation medium with containing xylose mother liquor, and controlled the initial OD 600 nm of 0.1. After fermenting to the log phase at 30° C., 100 rpm, the fermentation broth was added $CaCO_3$ with a final concentration of 10 g/L. Samples at certain intervals of the fermentation broth were tested for the OD 600 nm and pH. And the fermentation broths at different time points were collected to detect the content of glucose, ethanol, ethylene glycol and xylonic acid with the help of HPLC as the same steps above. As shown in FIG. 6A and FIG. 6B, 1.6 g/L ethylene glycol could be produced in the recombinant strain EG2.

The above is only the preferred embodiments of this disclosure and is not intended to limit this disclosure. Any modification, equivalent replacement, improvement, etc., made within the spirit and principle of this disclosure shall be included in the scope of this disclosure.

What is claimed is:

1. A recombinant *Zymomonas mobilis* strain for producing ethylene glycol, wherein the recombinant strain is a *Zymomonas mobilis* transformed with a recombinant plasmid, wherein the recombinant plasmid comprises a xdh gene, a yagF gene, a yagE gene and a ZMO1771 gene, wherein the nucleotide sequence of the xdh gene is the nucleotide sequence set forth in SEQ ID NO: 1, the nucleotide sequence of the yagF gene is the nucleotide sequence set forth in SEQ ID NO: 9, the nucleotide sequence of the yagE gene is the nucleotide sequence set forth in SEQ ID NO: 10, and the nucleotide sequence of the ZMO1771 gene is the nucleotide sequence set forth in SEQ ID NO: 15.

2. A method of preparing a recombinant *Zymomonas mobilis* strain for producing ethylene glycol comprising:
    preparing a recombinant plasmid, wherein the recombinant plasmid comprises a xdh gene, a yagF gene, a yagE gene and a ZMO1771 gene, wherein the nucleotide sequence of the xdh gene is the nucleotide sequence set forth in SEQ ID NO: 1, the nucleotide sequence of the yagF gene is the nucleotide sequence set forth in SEQ ID NO: 9, the nucleotide sequence of the yadE gene is the nucleotide sequence set forth in SEQ ID NO: 10, and the nucleotide sequence of the ZMO1771 gene is the nucleotide sequence set forth in SEQ ID NO: 15, wherein the xdh gene is expressed under the control of a Ppdc promoter, wherein the yagF gene, the yagE gene, and the ZMO1771 gene are linked by a ribosome binding sequence and expressed under the control of a Peno promoter; and
    transforming a *Zymomonas mobilis* with the recombinant plasmid, thereby preparing a recombinant *Zymomonas mobilis* strain for producing ethylene glycol.

3. A method of producing ethylene glycol comprising the steps of:
    fermenting the recombinant *Zymomonas mobilis* strain of claim 1 in a fermentation medium to produce a fermentation broth comprising ethylene glycol; and
    filtering the fermentation broth after centrifugation to obtain the ethylene glycol.

* * * * *

SEQUENCE LISTING

```
Sequence total quantity: 32
SEQ ID NO: 1            moltype = DNA  length = 807
FEATURE                 Location/Qualifiers
source                  1..807
                        mol_type = other DNA
                        organism = Paraburkholderia xenovorans
SEQUENCE: 1
atgtatctgt tgagctatcc ggaacaggtt gattatccga tgtcctatgc catttatccg   60
agcttgtccg gtaaaaccgt tgttattacc ggtggtggtt ccggtattgg tgccgctatg  120
gttgaagcct tgcccgtca gggtgctcgt gttttcttcc ttgatgttgc tgaagatgat  180
tctttggctt tgcagcagtc tttgtctgat gctccgcatc cgccgttgtt tcgtcgttgt  240
gatcttcgtt ctgttgatgc tattcattct gcttttgccg gtattgttga aattgccggt  300
cctattgaag ttttggttaa taatgccggt aatgatgatc gtcatgaagt tgatgctatc  360
accctgcct attgggatga acgtatggct gttaatttgc gtcatcagtt cttctgtgcc  420
caggcggctg cggctggtat gcgtaaaatc ggtcgtggtg ttatttgaa tttgggctct  480
gtttcttggc atttggcttt gccgaatttg gctatttata tgtctgccaa agctggtatt  540
gaaggtttga cgcgtggtct tgcccgtgat ttgggtgctg ccggtatccg tgttaattgt  600
attattccgg gtgccgttcg tacgccgcgt caaatgcagt tgtggcagtc tccggaatct  660
gaagccaaat tggttgcctc tcagtgtttg cgtttgcgta ttgaacctga acatgttgcc  720
cgtatggctt tgtttttggc ctctgatgat gcgtctcgtt gttctggtcg tgattatttt  780
gttgatgctg gttggtatgg tgaataa                                       807

SEQ ID NO: 2            moltype = DNA  length = 199
FEATURE                 Location/Qualifiers
source                  1..199
                        mol_type = other DNA
                        organism = unidentified
SEQUENCE: 2
tatcgctcat gatcgcggca tgttctgata ttttcctct aaaaagata aaagtctttt    60
tcgcttcggc agaagaggtt catcatgaac aaaaattcgg cattttaaa aatgcctata  120
gctaaatccg gaacgacact ttagaggttt ctgggtcatc ctgattcaga catagtgttt  180
tgaatatatg gagtaagca                                                199

SEQ ID NO: 3            moltype = DNA  length = 41
FEATURE                 Location/Qualifiers
source                  1..41
                        mol_type = other DNA
                        organism = synthetic construct
SEQUENCE: 3
attcgcggcc gcttctagag tatcgctcat gatcgcggca t                       41

SEQ ID NO: 4            moltype = DNA  length = 57
FEATURE                 Location/Qualifiers
source                  1..57
                        mol_type = other DNA
                        organism = unidentified
SEQUENCE: 4
```

```
ggatagctca acagatacat tgcttactcc atatattcaa aacactatgt ctgaatc         57

SEQ ID NO: 5           moltype = DNA   length = 27
FEATURE                Location/Qualifiers
source                 1..27
                       mol_type = other DNA
                       organism = synthetic construct
SEQUENCE: 5
atgtatctgt tgagctatcc ggaacag                                           27

SEQ ID NO: 6           moltype = DNA   length = 31
FEATURE                Location/Qualifiers
source                 1..31
                       mol_type = other DNA
                       organism = synthetic construct
SEQUENCE: 6
ttattcacca taccaaccag catcaacaaa a                                      31

SEQ ID NO: 7           moltype = DNA   length = 17
FEATURE                Location/Qualifiers
source                 1..17
                       mol_type = other DNA
                       organism = synthetic construct
SEQUENCE: 7
gtaaaacgac ggccagt                                                      17

SEQ ID NO: 8           moltype = DNA   length = 17
FEATURE                Location/Qualifiers
source                 1..17
                       mol_type = other DNA
                       organism = synthetic construct
SEQUENCE: 8
gtcatagctg tttcctg                                                      17

SEQ ID NO: 9           moltype = DNA   length = 1968
FEATURE                Location/Qualifiers
source                 1..1968
                       mol_type = other DNA
                       organism = Escherichia coli
SEQUENCE: 9
atgaccattg agaaattttt caccccgcag gacgacgcgt tttatgcggt gatcacccac       60
gcggcggggc cgcagggcgc tctgccgctg acccccgaga tgctgatgga atctcccagc      120
ggcaacctgt tcggcatgac gcagaacgcc gggatgggct gggacgccaa caagctcacc      180
ggcaaagagg tgctgattat cggcactcag ggcggcatcc gcgccggaga cggacgccca      240
atcgcgctgg gctaccacac cgggcattgg gagatcggca tgcagatgca ggcggcggcg      300
aaggagatca cccgcaatgg cgggatcccg ttcgcggcct cgtcagcga tccgtgcgac       360
gggcgctcgc agggcacgca cggtatgttc gattcccgtc cgtaccgcaa cgacgcggcg      420
atcgtgtttc gccgcctgat ccgctccctg ccgacgcggc gggcggtgat cggcgtagcg      480
acctgcgata aagggctgcc cgccaccatg attgcgctgg ccgcgatgca cgacctgccg      540
actattctgg tgccggggcg gcgacgctg ccgccgaccg tcggggaaga cgcgggcaag       600
gtgcagacca tcggcgcgcg tttcgccaac cacgaactct ccctgcagga ggccgccgaa      660
ctgggctgtc cgcgcctgcg ctcgccgggc ggcgggtgtc agttcctcgg cacggcgggc      720
acctcgcagg tggtcgcgga ggcgctgggt ctggcgctgc cgcactccgc gctggcgccg      780
tccgggcagg cggtgtggct ggagatcgcc gccagtcgg cgcgcgcggt cagcgagctg       840
gatagccgcg gcatcaccac gcgggatatc ctctccgata aagccatcga aaacgcgatg      900
gtgatccacg cggcgttcgg ggctccacc aatttactgc tgcacattcc ggccatcgcc       960
cacgcggcgg gctgcacgat cccggacgtt gagcactgga cgcgcatcaa ccgtaaagtg     1020
ccgcgtctgt tgagcgtgct gcccaacggc cggactatc acccgaccgt gcgcgccttc      1080
ctcgcgggcg gcgtgccgga ggtgatgctc cacctgcgcg acctcggcct gctgcatctg     1140
gacgccatga ccgtgaccgg ccagacggtg ggcgagaacc ttgaatggtg gcaggcgtcc     1200
gagcgccggg cgcgcttccg ccagtgcctg cgcgagcagg acggcgtaga gccggatgac     1260
gtgatcctgc cgccggagaa ggcaaaagcg aaagggctga cctcgacggt ctgcttcccg     1320
acgggcaaca tcgctccgga aggttcggtg atcaaggcca cggcgatcga cccgtcggtg     1380
gtgggcgaag atgcgtata ccaccacacc ggcgggtgt tgtttttgt ctcggaagcg        1440
caggcgatca aggcgatcaa gcgggaagag attgtgcagg gcgatatcat ggtggtgatc     1500
ggcggcgggc cgtccggcac cggcatggaa gagacctacc agctcacctc cgcgctaaag     1560
catatctcgt ggggcaagac ggtgtcgctc atcaccgatg cgccgcttctc gggcgtgtcg    1620
acgggcgcct gcttcggcca cgtgtcgccg gaggcgctgg cgggcgggcc gattggcaag     1680
ctgcgcgata acgacatcat cgagattgcc gtggatcgtc tgacgttaac tggcagcgtg     1740
aacttcatcg gcaccgcgga caacccgctg acgccggaag agggcgcgcg cgagctggcg     1800
cggcggcaga cgcaccccgga cctgcacgcc cacgactttt tgccggacga cacccggctg     1860
tgggcggcac tgcagtcggt gagcggcggc acctggaaag ctgtatttta tgacaccgat     1920
aaaattatcg aggtaattaa cgccggtaaa aaagcgctcg gaattttaa                 1968

SEQ ID NO: 10          moltype = DNA   length = 909
FEATURE                Location/Qualifiers
source                 1..909
                       mol_type = other DNA
                       organism = unidentified
```

```
SEQUENCE: 10
atgccgcagt ccgcgttgtt cacgggaatc attccccctg tctccaccat ttttaccgcc    60
gacggccagc tcgataagcc gggcaccgcc gcgctgatcg acgatctgat caaagcaggc   120
gttgacggcc tgttcttcct gggcagcggt ggcgagttct cccagctcgg cgccgaagag   180
cgtaaagcca ttgcccgctt tgctatcgat catgtcgatc gtcgcgtgcc ggtgctgatc   240
ggcaccggcg gcaccaacgc ccgggaaacc atcgaactca gccagcacgc gcagcaggcg   300
ggcgcggacg gcatcgtggt gatcaaccec tactactgga aagtgtcgga agcgaacctg   360
atccgctatt tcgagcaggt ggccgacagc gtcacgctgc cggtgatgct ctataacttc   420
ccggcgctga ccgggcagga tctgactccg gcgctggtga aaaccctgcc cgactcgcgc   480
agcaatatta tcggcatcaa agacaccatc gactccgtcg cccacctgcg cagcatgatg   540
cataccgtca aaggtgccca tccgcacttc accgtgctct gcggctacga cgatcatctg   600
ttcaataccc tgctgctcgg cggcgacggg gcgatatcgg cgagcggcaa ctttgccccg   660
caggtgtcgg tgaatcttct gaaagcctgg cgcgacgggg acgtggcgaa agcggccggg   720
tatcatcaga ccttgctgca aattccgcag atgtatcggc tggatgaggc gtttgtgaac   780
gtgattaaag aggcgatcgt gctctgcggt cgtcctgtct ccacgcacgt gctgccgccc   840
gcctcgccgc tggacgagcc gcgcaaggcg cagctgaaaa ccctgctgca acagctcaag   900
ctttgctga                                                           909

SEQ ID NO: 11         moltype = DNA  length = 1164
FEATURE               Location/Qualifiers
source                1..1164
                      mol_type = other DNA
                      organism = Escherichia coli
SEQUENCE: 11
atgaacaact ttaatctgca cacccaacc cgcattctgt ttggtaaagg cgcaatcgct    60
ggtttacgcg aacaaattcc tcacgatgct cgctattga ttacctacgg cggcggcagc   120
gtgaaaaaa ccggcgttct cgatcaagtt ctggatgccc tgaaaggcat ggacgtgctg   180
gaatttggcg gtattgagcc aaaccccggct tatgaaacgc tgatgaacgc cgtgaaactg   240
gttcgcgaac agaaagtgac tttcctgctg gcggttggcg gcggttctgt actggacggg   300
accaaattta tcgccgcagc ggctaactat ccggaaaata tcgatccgtg gcacattctg   360
caaacgggcg gtaaagagat taaaagcgcc atcccgatgg gctgtgtgct gacgctgcca   420
gcaaccggtt cagaatccaa cgcaggcgcg gtgatctccc gtaaaaccac aggcgacaag   480
caggcgttcc attctgccca tgttcagccg gtatttgccg tgctcgatcc ggtttatacc   540
tacaccctgc cgccgcgtca ggtggctaac ggcgtagtgg acgcctttgt acacaccgtg   600
gaacagtatg ttaccaaacc ggttgatgcc aaaattcagg accgtttcgc agaaggcatt   660
ttgctgacgc taatcgaaga tggtccgaaa gcccctgaaag agccagaaaa ctacgatgtg   720
cgcgccaacg tcatgtgggc ggcgactcag gcgctgaacg tttgattgg cgctggcgta   780
ccgcaggact gggcaacgca tatgctgggc acgaactga ctgcgatgca cggtctggat   840
cacgcgcaaa cactgctat cgtcctgcct gcactgtgga atgaaaacg cgataccaag   900
cgcgctaagc tgctgcaata tgctgaacgc gtctggaaca tcactgaagg ttccgatgat   960
gagcgtattg acgccgcgat tgccgcaacc cgcaatttct ttgagcaatt aggcgtgccg  1020
acccacctct ccgactacgg tctggacggc agctccatcc cggcttttgct gaaaaaactg  1080
gaagagcacg gcatgaccca actgggcgaa aatcatgaca ttacgttgga tgtcagccgc  1140
cgtatatacg aagccgcccg ctaa                                         1164

SEQ ID NO: 12         moltype = DNA  length = 1776
FEATURE               Location/Qualifiers
source                1..1776
                      mol_type = other DNA
                      organism = unidentified
SEQUENCE: 12
atgagcaatc gcaccccgcg tcgtttttcgc agccgtgatt ggtttgataa tccggatcat    60
attgatatga ccgccttgta tttggaacgc tttatgaatt atggtatcac cccggaagaa   120
ttacgttctg gcaaacctat tattggtatt gcccagacgg ttctgatat ttctccttgt   180
aatcgtattc atttggattt ggttcagcgg gttcgggatg gtattcgcga tgccggtggt   240
attcctatgg aatttccggt tcatccatt ttcgaaaatt gtcgtcgtcc gacggccgcc   300
ttagatcgta atttgtctta tttgggtttg gttgaaacgt tgcatggtta tccgattgat   360
gccgttgttt tgaccaccgg ttgtgataaa accaccccctg ccggtattat ggctgccacc   420
accgttaata ttcctgccat tgttctttct ggtgtgcccga tgttgatgg ttgcatgaa   480
aatgaattgg ttggctctgg cacggtcatt tggcgttctc gtcgtaaatt ggccgccggt   540
gaaatcaccg aagaagaatt tattgatcgt gctgcttctt ctgctccgtc tgccggtcat   600
tgtaatacca tgggtaccgc ctctaccatg aatgccgttg ccgaagcctt gggttttgtct   660
ttaaccggtt gtgctgccat tccggcccct tatcgtgaac gtggtcagat ggcctataaa   720
accggccagc gtattgtcga tttgcgtat gatgatgtta aacgttgga tatttgaaa   780
aaacaggctt tgaaaatgc tattgccttg gttgccgccg ctggtggttc taccaatgcc   840
caaccgcata ttgttgccat ggcccgtcat gctggtgtcg aaattaccgc cgatgattgg   900
cgtgccgctt atgatattcc gttgattgtt aatatgcagc cggcgggtaa atatttaggt   960
gaacgtttc atccgtcggg tggtgcccct gctgttttgt gggaattgtt gcagcaggtt  1020
cgtttgcatg gtttttttt gacggttacg ggtaaaacca tgtctgaaaa tttgcagggt  1080
cgtgaaacct ctgatcgtga agttatttc ccgtatcatg aaccgcttgc gaaaaggccc  1140
ggtttttttgg ttttgaaagg taatttgttt gattttgcca tcatgaaaag ctctgttatt  1200
ggtgaagaat tcgtaaacg ttatttgtct cagccgggtc aggaaggtgt tttcgaagct  1260
cgtgccattg ttttcgatgg ttctgatgat tatcataaac gtatcaatga tccggccttg  1320
gaaattgatg aacgtatt tttggtcatt cgtggtggtc gtccgattgg ttgccggggt  1380
tctgctgaag ttgttaatat gcaaccgccg gatcattgt tgaagaaggg tattatgtct  1440
ttgccgaccct gggtgatgg tcgtcagtct ggtacggccg attctccgtc tattttgaat  1500
gcctctcctg aaagcgccat cggtggtggt ttatcttggt tgcgtacggg tgataccatt  1560
cgtattgatt tgaatacggg tcgttgtgat gccttggttg atgaagccac cattgccgcc  1620
cgcaaacagg atggtattcc ggctgttcct gctacgatga ccccgtggca agaaatttat  1680
```

```
cgtgctcatg ccagccagtt agatacgggt ggtgttttgg aatttgccgt caaatatcaa  1740
gatttggcgg ctaaattgcc gcgtcataat cattaa                            1776
```

SEQ ID NO: 13           moltype = DNA  length = 1968
FEATURE                 Location/Qualifiers
source                  1..1968
                        mol_type = other DNA
                        organism = Escherichia coli
SEQUENCE: 13
```
atgtctgttc gcaatatttt tgctgacgag agccacgata tttacaccgt cagaacgcac   60
gccgatggcc cggacggcga actcccatta accgcagaga tgcttatcaa ccgcccgagc  120
ggggatctgt tcggtatgac catgaatgcc ggaatgggtt ggtctccgga cgagctggat  180
cgggacggta ttttactgct cagtacactc ggtggcttac gcggcgcaga cggtaaaccc  240
gtggcgctgg cgttgcacca ggggcattac gaactggaca tccagatgaa agccgcggcg  300
gaggttatta aagccaacca tgccctgccc tatgccgtgt acgtctccga tccttgtgac  360
gggcgtactc agggtacaac ggggatgttt gattcgctac cataccgaaa tgacgcatcg  420
atggtaatgc gccgccttat tcgctctctg cccgacgcga aagcagttat tggtgtggcg  480
agttgcgata aggggcttcc ggccaccatg atggcactgc ccgcgcagca caacatcgca  540
accgtgctgg tccccggcgg cgcgacgctg cccgcaaagg atggagaaga caacggcaag  600
gtgcaaacca ttggcgcacg cttgccaatg gcgaattat  ctctacagga cgcacgcgt   660
gcgggctgta aagcctgtgc ctcttccggc ggcggctgtc aattttgggg cactgccggg  720
acatctcagg tggtggccga aggattggga ctggcaatcc acattcagc cctggcccct  780
tccggtgagc ctgtgtggcg ggagatcgcc agagcttccg cgcgagctgc gctgaacctg  840
agtcaaaaag gcataccacc ccgggaaatt ctcaccgata aagcgataga gaatgcgatg  900
acggtccatg ccgcgttcgg tggttcaaca aacctgctgt tacacatccc ggcaattgct  960
caccaggcag gttgccatat cccgaccgtt gatgactgga tccgcatcaa caagcgcgtg 1020
ccccgactgg tgagcgtact gcctaatggc ccgtttatc  atccaacggt caatgccttt 1080
atggcaggtg tgtgccggaa agtcatgttg catctgcgca gcctcggatt gttgcatgaa 1140
gacgttatga cggttaccgg cagcacgctg aaagaaaacc tcgactggtg ggagcactcc 1200
gaacggcgtc agcggttcaa gcaactcctg ctcgatcagg aacaaatcaa cgctgacgaa 1260
gtgatcatgt ctccgcagca agcaaaagcg cgcggattaa cctcaactat caccttcccg 1320
gtgggcaata ttgcgccaga aggtcgggtg atcaaatcca ccgccattga ccctcgatg  1380
attgatgagc aaggtatcta ttaccataaa ggtgtggcga aggtttatct gtccgagaaa 1440
agtgcgattt acgatatcaa acatgacaag atcaaggcgg gcgatattct ggtcattatt 1500
ggcgttggac cttcaggtac agggatggaa gaaacctacc aggttaccag tgccctgaag 1560
catctgtcat acggtaagca tgtttcgtta atcaccgatg cacgtttctc gggcgtttct 1620
actggcgcgt gatcggcca tgtggggcca gaagcgctgg ccgaggccc  atcggtaaa  1680
ttacgcaccg gggatttaat tgaaattaaa attgattgtc gcgagcttca cggcgaagtc 1740
aatttcctcg gaacccgtag cgatgaacaa ttaccttcac aggaggagc aactgcaata 1800
ttaaatgcca gacccagcca tcaggattta cttcccgatc ctgaattgcc agatgatacc 1860
cggctatggg caatgcttca ggccgtgagt ggtgggacat ggaccggttg tatttatgat 1920
gtaaacaaaa ttggcgcggc tttgcgcgat tttatgaata aaaactga              1968
```

SEQ ID NO: 14           moltype = DNA  length = 1149
FEATURE                 Location/Qualifiers
source                  1..1149
                        mol_type = other DNA
                        organism = Escherichia coli
SEQUENCE: 14
```
atggctaaca gaatgattct gaacgaaacg gcatggtttg gtcggggtgc tgttggggct   60
ttaaccgatg aggtgaaacg ccgtggttat cagaaggcgc tgatcgtcac cgataaaaca  120
ctggtgcaat gcggcgtggt ggcgaaagtg accgataaga tggatgctgc agggctggca  180
tgggcgattt acgacggcgt agtgcccaac ccaacaatta ctgtcgtcaa agaagggctc  240
ggtgtattcc agaatagcgg cgcggattac ctgatcgcta ttggtggtgg ttctccacag  300
gatacttgta aagcgattgg cattatcagc aacaaccgga agttgccga tgtgcgtagc  360
ctggaagggc ttcccccgac caataaaccc agtgtaccga ttctggcaat tcctaccaca  420
gcaggtactg cggcagaagt gaccattaac tacgtgatca ctgacgaaga gaacggcgc   480
aagtttgttt gcgttgatcc gcatgatatc ccgcaggtgg cgtttattga cgctgacatg  540
atggatggta tgcctccagc gctgaaagct gcgacgggtc tcgatgcgct cactcatgct  600
attgaggggt atattacccg tggcgcgtgg gcgctaaccg atgcactgca cattaaagcg  660
attgaaatca ttgctgggc  gctgcgagga tcggttgctg gtgataagga tgccggagaa  720
gaaatgcgc  tcgggcagta tgttgcgggt atgggcttct cgaatgttgg gttagggttg  780
gtgcatggta tggcgcatcc actgggcgcg ttttataaca ctccacacgg tgttgcgaac  840
gccatcctgt taccgcatgt catgcgttat aacgctgct  ttaccggtga gaagtaccgc  900
gatatcgcgc gcgttatggg cgtgaaagtg gaaggtatga gcctggaaga ggcgcgtaat  960
gccgctgttg aagcggtgtt tgctctcaac cgtgatgtcg gtattccgcc acatttcgct 1020
gatgttggtg tacgcaagga agacattccg gcactggcgc aggcggcact ggatgatgtt 1080
tgtaccggtg gcaacccgcg tgaagcaacg cttgaggata ttgtagagct ttaccatacc 1140
gcctggtaa                                                         1149
```

SEQ ID NO: 15           moltype = DNA  length = 1158
FEATURE                 Location/Qualifiers
source                  1..1158
                        mol_type = other DNA
                        organism = Zymomonas mobilis
SEQUENCE: 15
```
atgctcaatt ttgattatta taatccgacc catattgttt ttggtaaagg ccgtattgca   60
cagcttgata cgctttttgtc gaaagatgcc cgtgttttag tcctttatgg cggttctagc  120
gctcaaaaga ccggcactt  ggatgaagtc agaaaagccc ttggtgaccg cacttatttt  180
```

-continued

```
gaatttggtg gtatcgaacc caatcccagc tatgaaactc tgatgaaagc cgtcgagcag    240
gtcaaacagg aaaaggttga ttttctgttg gctgttgggg gtggatcagt cattgatggc    300
accaaattcg tagcagccgc cgtgccttat gaaggtgagc cttgggaaat tctgaaaacg    360
gatggcaaga aaatcaagga agccttgccc gttggaaccg ttttaaccct gccggctacc    420
ggctccgaaa tgaaccggaa tagtgtggta acccgcagct caatcaaatc gaaacggggt    480
ttccataatg accatgtttt tccggttttc tcgattcttg acccgacaaa ggtttacact    540
ttgccgccgc gccagctggc aaatgggggtt gtcgattcct ttattcatat caccgaacaa    600
tatctgacct atccggttga tggtatggtt caggatgaat ttgcagaagg tctgctccgc    660
accttaatca aaattggccc tgaattgctg aaagatcaga agaattatga tctagccgcc    720
aattttatgt ggacggcgac cttggctttg aatggcttga tcggtgccgg tgtgccacag    780
gattgggcaa cccatatggt cggtcatgaa ttgacggccg cctttggtat cgatcatggt    840
cggacattgg cgattattct ccctttcgctg ttgcaaaatc agagagaggc caagaaaggc    900
aagctgctgc aaatatgccaa gaatgtttgg catattgatc agggctctga tgatgaacgg    960
attgatgccg caatcgaaaa gactcgtcat ttctttgaat cattaggtat tccgacccat   1020
ctgaaagatt atgatgttgg ggaagagtct attgatatgc tggtcaagga attagaagcg   1080
catggcatgt cccagctagg cgaacataag gctattacgc cagaggttag ccgcgctatt   1140
ctgcttgcaa gcttgtaa                                                1158

SEQ ID NO: 16           moltype = DNA   length = 201
FEATURE                 Location/Qualifiers
source                  1..201
                        mol_type = other DNA
                        organism = unidentified
SEQUENCE: 16
tgtctatact ccagttactc aatacgtaac aataatcagt ttatcctaac tatagaatcg     60
catgagaagc gataacgttt caccataagc aatatattca ttgcaacagt ggaattgcct    120
tatgcgtcaa ggaaggatag atcattgacg gactgagttc aaaaagagac tcgtctaaaa    180
gattttaaga aaggtttcga t                                              201

SEQ ID NO: 17           moltype = DNA   length = 50
FEATURE                 Location/Qualifiers
source                  1..50
                        mol_type = other DNA
                        organism = synthetic construct
SEQUENCE: 17
tgtctatact ccagttactc aatacgtaac aataatcagt ttatcctaac                50

SEQ ID NO: 18           moltype = DNA   length = 32
FEATURE                 Location/Qualifiers
source                  1..32
                        mol_type = other DNA
                        organism = synthetic construct
SEQUENCE: 18
atcgaaacct tcttaaaat cttttagacg ag                                   32

SEQ ID NO: 19           moltype = DNA   length = 47
FEATURE                 Location/Qualifiers
source                  1..47
                        mol_type = other DNA
                        organism = synthetic construct
SEQUENCE: 19
attttaagaa aggtttcgat atgaccattg agaaaatttt caccccg                  47

SEQ ID NO: 20           moltype = DNA   length = 46
FEATURE                 Location/Qualifiers
source                  1..46
                        mol_type = other DNA
                        organism = synthetic construct
SEQUENCE: 20
ggcattttct cctctttaat ttaaattccg agcgcttttt taccgg                   46

SEQ ID NO: 21           moltype = DNA   length = 38
FEATURE                 Location/Qualifiers
source                  1..38
                        mol_type = other DNA
                        organism = synthetic construct
SEQUENCE: 21
tttaaattaa agaggagaaa atgccgcagt ccgcgttg                            38

SEQ ID NO: 22           moltype = DNA   length = 43
FEATURE                 Location/Qualifiers
source                  1..43
                        mol_type = other DNA
                        organism = synthetic construct
SEQUENCE: 22
ttcattttct cctctttaat tcagcaaagc ttgagctgtt gca                      43

SEQ ID NO: 23           moltype = DNA   length = 46
FEATURE                 Location/Qualifiers
```

```
source                          1..46
                                mol_type = other DNA
                                organism = synthetic construct
SEQUENCE: 23
gctgaattaa agaggagaaa atgaacaact ttaatctgca caccccc              46

SEQ ID NO: 24                   moltype = DNA   length = 40
FEATURE                         Location/Qualifiers
source                          1..40
                                mol_type = other DNA
                                organism = synthetic construct
SEQUENCE: 24
cagcggccgc tactagttta gcgggcggct tcgtatatac                      40

SEQ ID NO: 25                   moltype = DNA   length = 38
FEATURE                         Location/Qualifiers
source                          1..38
                                mol_type = other DNA
                                organism = synthetic construct
SEQUENCE: 25
attttaagaa aggtttcgat atgagcaatc gcaccccg                        38

SEQ ID NO: 26                   moltype = DNA   length = 48
FEATURE                         Location/Qualifiers
source                          1..48
                                mol_type = other DNA
                                organism = synthetic construct
SEQUENCE: 26
ggcattttct cctctttaat ttaatgatta tgacgcggca atttagcc              48

SEQ ID NO: 27                   moltype = DNA   length = 48
FEATURE                         Location/Qualifiers
source                          1..48
                                mol_type = other DNA
                                organism = synthetic construct
SEQUENCE: 27
attttaagaa aggtttcgat atgtctgttc gcaatatttt tgctgacg              48

SEQ ID NO: 28                   moltype = DNA   length = 51
FEATURE                         Location/Qualifiers
source                          1..51
                                mol_type = other DNA
                                organism = synthetic construct
SEQUENCE: 28
ggcattttct cctctttaat tcagttttta ttcataaaat cgcgcaaagc c          51

SEQ ID NO: 29                   moltype = DNA   length = 50
FEATURE                         Location/Qualifiers
source                          1..50
                                mol_type = other DNA
                                organism = synthetic construct
SEQUENCE: 29
gctgaattaa agaggagaaa atggctaaca gaatgattct gaacgaaacg            50

SEQ ID NO: 30                   moltype = DNA   length = 43
FEATURE                         Location/Qualifiers
source                          1..43
                                mol_type = other DNA
                                organism = synthetic construct
SEQUENCE: 30
cagcggccgc tactagttta ccaggcggta tggtaaagct cta                   43

SEQ ID NO: 31                   moltype = DNA   length = 57
FEATURE                         Location/Qualifiers
source                          1..57
                                mol_type = other DNA
                                organism = synthetic construct
SEQUENCE: 31
gctgaattaa agaggagaaa atgctcaatt ttgattatta taatccgacc catattg    57

SEQ ID NO: 32                   moltype = DNA   length = 42
FEATURE                         Location/Qualifiers
source                          1..42
                                mol_type = other DNA
                                organism = synthetic construct
SEQUENCE: 32
cagcggccgc tactagttta caagcttgca agcagaatag cg                    42
```